United States Patent [19]

Vaillancourt

[11] Patent Number: 4,760,847
[45] Date of Patent: Aug. 2, 1988

[54] DEPTH MEASURING DEVICE

[76] Inventor: Vincent Vaillancourt, 14 Bunyan Dr., Livingston, N.J. 07039

[21] Appl. No.: 897,747

[22] Filed: Aug. 18, 1986

[51] Int. Cl.⁴ ............................................. A61B 17/34
[52] U.S. Cl. ............................... 128/329 R; 128/907; 128/737; 604/117; 604/192; 33/169 B
[58] Field of Search .......... 128/303 R, 329 A, 329 R, 128/907, 737, 744, 774, 778; 33/169 B, 483, 493, 511, 545; 604/192–198, 117

[56] References Cited

U.S. PATENT DOCUMENTS

| | | | |
|---|---|---|---|
| 750,449 | 1/1904 | Gillard | 33/169 B |
| 1,327,114 | 1/1920 | Rhein | 33/169 B |
| 2,091,438 | 8/1937 | Epstein | 604/117 |
| 2,763,935 | 9/1956 | Whatley et al. | 128/774 |
| 3,230,628 | 1/1966 | Hite | 33/483 |
| 3,478,435 | 11/1969 | Cook | 33/169 B |
| 3,706,307 | 12/1972 | Hasson | 128/778 |
| 3,905,375 | 9/1975 | Toyama | 128/329 A |
| 4,216,585 | 8/1980 | Hatter | 33/169 B |
| 4,505,278 | 3/1985 | Alban | 128/774 |

Primary Examiner—Stephen C. Pellegrino
Assistant Examiner—Ralph Lewis
Attorney, Agent, or Firm—Kenyon & Kenyon

[57] ABSTRACT

The depth measuring device employs a solid needle with a slidable rider as well as a transparent tube which is provided with a graduated scale and a closed bottom or marking lines. During penetration through the skin into a vascular implant device, the rider slides along the needle. When the needle is returned into the transparent tube and properly seated, with the end of the needle on the bottom or at the marking lines, the position of the rider can be read from the scale to indicate the depth of penetration of the needle. An appropriately sized right-angled Huber needle can then be selected for use with the implanted device.

13 Claims, 1 Drawing Sheet

DEPTH MEASURING DEVICE

This invention relates to a depth measuring device. More particularly, this invention relates to a disposable depth measuring device for medical use.

As is known, patients are frequently provided with vascular access devices which are implanted under the skin in order to provide for repeated access to a blood vessel over extended periods of time. For example for prolonged drug and fluid administration such devices usually include a port which is closed over by a self-sealing septum which can be penetrated by a needle. Generally, in order to connect an administration set or like equipment to such a vascular access device for delivering a fluid into the device, use has been made of Huber needles and particularly, Huber needles with a right-angle bend to provide a leg which can penetrate through the skin of the patient into an implanted vascular access device as well as a second leg which may lie flat against the skin. However, in many cases, the penetrating leg of the right-angled Huber needles are not of the proper length so as to penetrate accurately into a vascular access device. This is due to the fact that the skin layers from patient-to-patient may be of different thickness or the access devices may be implanted at different depths. For example, if the penetrating leg of the right-angled Huber needle is too long, the leg will bottom on the vascular access device prior to full penetration. Hence, the second leg of the needle will not be able to lie flat against the skin of the patient. In the event that the penetrating leg is too short, there is a possibility that the leg may not penetrate the septum so that medication is not delivered to the access device for subsequent delivery into the blood vessel of the patient.

In the past, a trial and error technique has been used to select the appropriate right-angled Huber needle for use with an implanted vascular access device. In this regard, the needle is penetrated through the skin into the vascular access device and, if the needle does not bottom or bottoms excessively, another differently sized right-angled Huber needle is used. However, such a procedure is not efficient particularly where Huber needles are made to be disposable. Hence, once used, the needles must be discarded. Further, and more importantly, such a procedure is uncomfortable and disconcerting to a patient.

Accordingly, it is an object of the invention to provide a relatively simple structure for determining the proper depth of a vascular access device within a patient.

It is another object of the invention to provide a relatively simple disposable measuring device for determining the depth of a vascular access device in a patient.

It is another object of the invention to provide a depth measuring device which can be readily used and discarded after use.

Briefly, the invention provides a depth measuring device for an implanted vascular access device which comprises a straight needle having a sharp end for penetrating through a skin layer into and bottoming on an implanted vascular access device, a rider which is slidably mounted on the needle and means having a graduated scale for measuring the distance from the sharp end of the needle to the rider after withdrawal of the needle from the vascular access device.

The needle is of solid construction to avoid coring of the septum of an access device and has a sharp end formed in any known fashion for penetrating through the skin of a patient.

The rider is in the form, for example, of a simple ring which is slidably mounted on the needle and which is initially positioned near the sharp end of the needle. During penetration through the skin of a patient, the rider slides along the needle away from the sharp end and, thus, acts as an indication of the distance from the sharp end to the outside surface of the skin of the patient The means for measuring the distance from the end of the needle to the rider includes a sleeve in the form of a transparent tube for receiving the needle and a peripheral marking on the tube for establishing the position of the end of the needle The graduated scale extends from this peripheral marking so that when the needle is inserted into the tube with the end positioned with respect to the peripheral marking, the position of the rider on the needle relative to the scale indicates the depth of penetration of the needle through the skin.

For ease of use, the graduated scale is formed as a series of circumferential lines on the transparent tube with appropriate indicia indicating the values of the lines. In addition, the peripheral marking for establishing the position of the sharp end of the needle within the tube may be in the form of a pair of concentric rings which are closely spaced apart. Thus, when the needle is inserted into the tube, alignment of the concentric rings with the eye of the viewer so that the rings appear as straight lines permits an accurate positioning of the needle.

In order to enhance the handling of the measuring device, the needle is mounted in a holder which is sized to fit into one end of the transparent tube to seal the tube at that end. The holder is also provided with a tubular finger grip, a cylindrical portion which is able to fit into the transparent tube and an annular shoulder at one end of the cylindrical portion to abut the open end of the transparent tube to accurately position the needle when taking a measurement.

In another embodiment, the means for measuring the distance of the rider from the end of the needle includes a wall at the closed end of the transparent tube against which the needle may bottom and from which the scale is measured. In this embodiment, a positive stop is provided to avoid a need to visually determine the position of the end of the needle.

In another embodiment, the means for measuring the distance of the rider from the sharp end of the needle may be in the form of a flat card having a slot for receiving the rider. In this case, the graduated scale extends from the slot. In use, after the needle has been inserted into a vascular access device and removed, the rider is placed in the slot with the needle extending from the slot along the graduated scale so that a measurement of the depth may be taken.

Where the transparent tube is provided with a closed end, the tube may act as a closed container to permit transportation and storage of the needle prior to use, and particularly, to maintain a sterilized state of the needle. The use of the tube as a container for the needle also enhances the disposability of the measuring device.

These and other objects and advantages of the invention will become more apparent from the following detailed description taken in conjunction with the accompanying drawings wherein.

Figure 1:
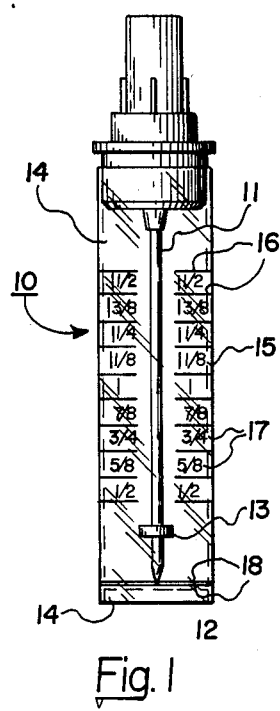
FIG. 1 illustrates a view of a depth measuring device in accordance with the invention.

Referring to FIG. 1, the depth measuring device 10 is formed as a disposable unit. In this regard, as shown in FIGS. 1 and 2, the device 10 includes a straight needle 11 of solid construction which has a sharp end 12 for penetrating through a skin layer of a patient and a rider 13, for example in the form of a rubber ring, which is slidably mounted on the needle 11.

The device 10 also has a means, for example, a sleeve in the form of a transparent plastic tube 14, having a graduated scale 15 for measuring the distance of the rider 13 from the needle end 12. The tube 14 has a wall to form a closed end at the bottom, as viewed, and an open end at the top. As indicated in FIGS. 1 and 2, the scale 15 is formed of a plurality of equi-spaced circumferential lines 16 of ink or suitable opague material along which indicia 17 are disposed for measuring purposes. In addition, the tube 14 has a peripheral marking, such as a pair of circumferential rings or locating lines 18 for establishing the position of an end of the needle 11 within the tube 14. As indicated in FIGS. 1 and 2, the peripheral markings 18 are made of an opaque ink similar to the lines 16 of the scale 15 and are closely spaced.

Figure 2:
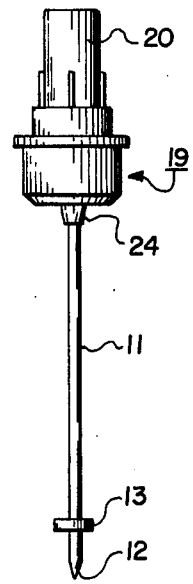
FIG. 2 illustrates an exploded view of the depth measuring device of FIG. 1.
Figure 3:
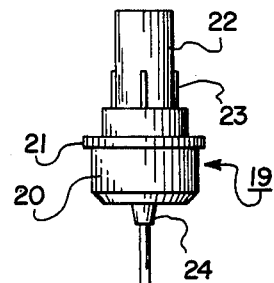
FIG. 3 illustrates a manner of using the needle and rider of the measuring device to establish the depth of penetration of the needle in accordance with the invention.

Referring to FIGS. 2 and 3, the needle 11 is secured, in a holder 19 which serves a dual function. That is, the holder 19 serves to position the needle 11 accurately within the tube 14 for measuring purposes and also functions to hold the needle 11 for penetrating into the skin of a patient.

The holder 19 includes a cylindrical mounting portion 20 which is sized to slide into the transparent tube 14 in a seal-tight manner, an annular shoulder 21 at the end of the cylindrical port 20 which acts as a stop to abut the end of the tube 14 and a tubular finger grip 22. This finger grip 22 is formed as a tube and is fixably but rotatably received in the mounting portion 20 via ribs 23. Also, the finger grip 22 is made of transparent material, and is necked-down at one end 24 to grip the needle 11 in fixed relation. At the other end, the finger grip 22 is spaced concentrically about the needle 11. This upper end of the finger grip 22 is of a larger diameter than the needle 11 in order to provide a substantial surface for gripping and holding the needle 11 for penetrating into the skin of the user. The necked-down end 24 of the grip 22 serves to seal the part of the needle 11 within the tube 14 against contamination from outside the tube prior to use.

As indicated in FIG. 1, the measuring device 10 is constructed so that the cylindrical portion 20 and the shoulder 21 of the holder 19 serve as a sealing cap for the plastic tube 14.

When the measuring device 10 is assembled, such is carried out in a sterile manner so that when the needle 11 and holder 19 unit is placed within the tube 14, the needle 11 is contained in a sealed environment. At the same time, the needle 11 is fabricated and/or the marking lines 18 on the tube 14 are positioned so that the sharp end 12 of the needle 11 which may be bevelled, is disposed in a plane of the lowermost line 18. At the same time, the rider 13 is mounted on the needle 11 at the lower end, for example between the scale 15 and the peripheral marking lines 18.

In order to use the measuring device 10, a nurse or other suitable person, grips the tubular finger grip 22 and pulls the needle 11 and holder 19 unit from the transparent tube 14 (FIG. 2). Next, the needle 11 is penetrated through the skin 25 of a patient (FIG. 3) into a vascular access device 26 implanted below the skin 25. The needle 11 penetrates until bottoming within a port of the device 26. During this time, the rider 13 initially abuts the outer surface of the skin 25 and, thereafter, slides along the length of the needle 11 during continued penetration of the needle 11 into the vascular access device 23. Once the needle 11 has bottomed, the distance between the end of the needle 11 and the rider 13 represents the depth of penetration.

The needle 11 is then withdrawn from the vascular access device 26 and skin 25 and returned into the transparent tube 14 (see FIG. 1). At this time, the needle 11 and holder 19 unit moves into the tube 14 until the tube 14 abuts the shoulder 21. The end 12 of the needle 11 is then within the confines of the peripheral marking lines 18, that is, with the end 12 of the needle 11 in the plane of the lowermost marking line 18. The position of the rider 13 relative to the graduated scale 15 then indicates the depth of penetration which can be visually read by the user so that the proper right angled Huber needle for feeding medication into the vascular access device 26 can be selected and subsequently implanted in the access device 26.

After obtaining the measurement for the depth of penetration of the needle 11, the measuring device 10 can be discarded. In this respect, the measuring device 10 is made of relatively few parts as well as of relatively inexpensive materials.

Figure 4:
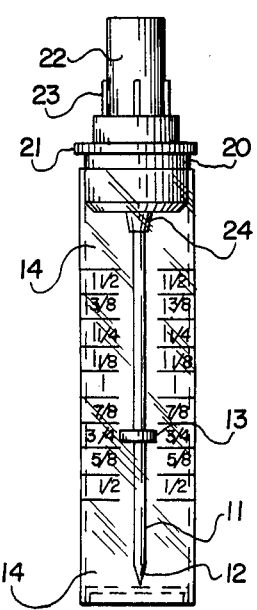
FIG. 4 illustrates a modified depth measuring device with the needle re-inserted into a transparent tube with a wall at a closed end to measure the penetration of a needle.

Alternatively, the marking lines 18 may be omitted and the wall 14' closing the bottom of the tube 14 may be used as a positive stop for the needle 11 with the scale 15 referenced thereto. In this case, after the needle 11 has been withdrawn from a patient, the needle 11 is inserted into the tube 14 to bring the sharp end 12 into abutment with the wall 14'. The position of the rider 13 relative to the scale 15 then indicates the depth of penetration as indicated in FIG. 4.

Figure 5:
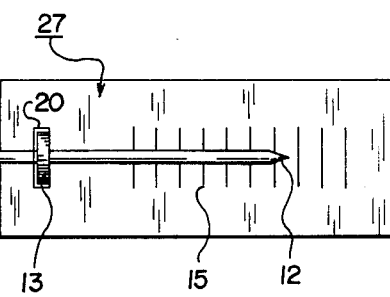
FIG. 5 illustrates a view of a modified depth measuring device in accordance with the invention.

Referring to FIG. 5, in another embodiment, instead of placing the graduated scale within a transparent tube 10, the scale 15 may be provided on a flat card 27. In this case, a slot 28 is also provided in the card 27 from which the scale 15 extends. After the needle 11 has penetrated into a vascular access device 26 as indicated in FIG. 3, the needle 11 and rider 13 can be laid on the card 27 in a manner so that the rider 13 is received in the slot 28 with the needle 11 extending along the scale 15. In this way, a measurement of the depth of penetration can be obtained since the scale 15 is related to the position of the slot 28, and thus, the position of the rider 13 from the sharp end 12 of the needle 11.

The invention thus provides a depth measuring device of relatively simple and inexpensive construction.

The use of a graduated scale 15 on the transparent tube 14 provides an easy mean of visually determining the position of the rider from the end of the needle and, thus the depth of penetration of the needle into an implanted vascular access device. Further, the tubular finger grip 22 of the holder 19 provides a firm surface which can be readily gripped and, along with the cylindrical portion 20, serves as a firm grip by which the needle 11 can be forced through the skin 25 into an access device 26.

Of note, the tube 14 into which the needle 11 and holder 19 unit is mounted may be cylindrical, as viewed, or may be of any other suitable cross sectional shape. Likewise, the mounting portion 20 may be of any suitable cross sectional shape to fit into a tube 14.

What is claimed is:

1. A depth measuring device for an implanted vascular access port comprising
    a holder;
    a straight needle of solid construction secured in said holder and having a sharp end for penetrating through a skin layer into and bottoming on an implanted vascular access port;
    a rider slidably mounted on said needle;
    a tube removably mounted on said holder over said needle, said tube being removable from said holder to expose said needle for penetration through a skin layer; and
    a graduated scale on said tube for measuring the distance of said rider to said sharp end of said needle after withdrawal of said needle from the vascular access port and remounting of said tube on said holder to indicate the depth of penetration of said needle into the vascular access port.

2. A depth measuring device as set forth in claim 1 wherein said tube includes a peripheral marking for establishing the position of said end of said needle within said tube and said scale extends from said marking.

3. A depth measuring device as set forth in claim 2 wherein said scale is formed of circumferential lines.

4. A depth measuring device as set forth in claim 1 wherein said tube includes a wall at one end for establishing the position of said end of said needle within said tube and said scale extends from said wall.

5. A depth measuring device comprising
    a holder;
    a needle secured in said holder and having a free projecting sharp end for penetrating a skin layer and bottoming on a vascular access port under the skin layer;
    a rider slidably mounted on said needle;
    a transparent tube removably mounted on said holder over said needle to expose said needle for penetration through a skin layer; and
    a scale on said tube for measuring the distance of said rider to said end of said needle after withdrawal of said needle from a vascular access port and remounting of said tube on said holder to indicate the depth of penetration of said needle into the vascular access port.

6. A depth measuring device as set forth in claim 5 wherein said rider is a ring.

7. A depth measuring device as set forth in claim 5 wherein said tube has a closed end for establishing the position of said end of said needle within said tube and said scale extends from said end.

8. A depth measuring device as set forth in claim 5 wherein said tube includes a peripheral marking for establishing the position of said end of said needle within said tube and said scale extends from said marking.

9. A depth measuring device as set forth in claim 8 wherein said marking is a pair of concentric rings.

10. A depth measuring device as set forth in claim 8 wherein said scale extends from said marking and is formed of circumferential lines.

11. A depth measuring device as set forth in claim 5 wherein said holder has a shoulder therein and said tube has one end abutting said shoulder.

12. A depth measuring device as set forth in claim 5 wherein said holder includes a cylindrical portion and a shoulder at one end of said portion and said tube is slidably mounted on said cylindrical portion and abutted against said shoulder.

13. A depth measuring device as set forth in claim 5 wherein said needle is of solid construction to avoid coring.

* * * * *